(12) United States Patent  
Daigle

(10) Patent No.: US 9,649,094 B2  
(45) Date of Patent: *May 16, 2017

(54) ULTRASOUND IMAGING SYSTEM WITH PIXEL ORIENTED PROCESSING

(71) Applicant: Verasonics, Inc., Redmond, WA (US)

(72) Inventor: Ronald Elvin Daigle, Redmond, WA (US)

(73) Assignee: Verasonics, Inc., Kirkland, WA (US)

( * ) Notice: Subject to any disclaimer, the term of this patent is extended or adjusted under 35 U.S.C. 154(b) by 151 days.

This patent is subject to a terminal disclaimer.

(21) Appl. No.: 14/707,383

(22) Filed: May 8, 2015

(65) Prior Publication Data

US 2016/0000407 A1    Jan. 7, 2016

Related U.S. Application Data

(63) Continuation of application No. 13/651,957, filed on Oct. 15, 2012, now Pat. No. 9,028,411, which is a (Continued)

(51) Int. Cl.
*A61B 8/00* (2006.01)
*A61B 8/08* (2006.01)
(Continued)

(52) U.S. Cl.
CPC .............. *A61B 8/5207* (2013.01); *A61B 8/06* (2013.01); *A61B 8/13* (2013.01); *A61B 8/14* (2013.01);
(Continued)

(58) Field of Classification Search
None
See application file for complete search history.

(56) References Cited

U.S. PATENT DOCUMENTS 5,396,890 A    3/1995    Weng
5,842,473 A    12/1998    Fenster et al.
(Continued)

FOREIGN PATENT DOCUMENTS

EP    1 790 384 A1    5/2007
FR    2 848 673 A1    12/2002
(Continued)

OTHER PUBLICATIONS

Office Action, mailed Apr. 12, 2011, for JP2008-506744, 3 pages.
(Continued)

*Primary Examiner* — Katherine Fernandez
*Assistant Examiner* — Farshad Negarestan
(74) *Attorney, Agent, or Firm* — Seed IP Law Group LLP

(57) ABSTRACT

An ultrasound imaging system with pixel oriented processing is provided in which an acoustic signal is generated, echoes from the acoustic signal are received at a plurality of receiving elements to obtain echo signals that are then stored, a given pixel is mapped into a region of the stored signals, the mapped region of the stored echo signals is organized into array for the given pixel after which the array is processed to generate a signal response for the given pixel to obtain acoustic information for the given pixel. The system can be implemented entirely on plug-in cards for a commercial PC motherboard. The system and method can be implemented for pixel-oriented or voxel-oriented image processing and display, eliminating intermediate data computations and enabling extensive use of software processing methods. Advantages include improved acquisition of signal dynamic range, flexible acquisition modes for high frame rate 2D, 3D, and Doppler blood flow imaging.

11 Claims, 15 Drawing Sheets

Related U.S. Application Data continuation of application No. 11/911,633, filed as application No. PCT/US2006/014096 on Apr. 14, 2006, now Pat. No. 8,287,456.

(60) Provisional application No. 60/671,416, filed on Apr. 14, 2005.

(51) Int. Cl.
   *A61B 8/06*   (2006.01)
   *A61B 8/13*   (2006.01)
   *G01S 7/52*   (2006.01)
   *A61B 8/14*   (2006.01)
   *G01S 15/89*  (2006.01)

(52) U.S. Cl.
   CPC ............ *A61B 8/4483* (2013.01); *A61B 8/466* (2013.01); *A61B 8/481* (2013.01); *A61B 8/483* (2013.01); *A61B 8/485* (2013.01); *A61B 8/488* (2013.01); *A61B 8/52* (2013.01); *A61B 8/5223* (2013.01); *G01S 7/5206* (2013.01); *G01S 7/52034* (2013.01); *G01S 7/5208* (2013.01); *G01S 7/52042* (2013.01); *G01S 15/8984* (2013.01); *G01S 15/8993* (2013.01); *G01S 15/8995* (2013.01)

(56) References Cited

U.S. PATENT DOCUMENTS

| | | | |
|---|---|---|---|
| 6,135,956 A | 10/2000 | Schmiesing et al. | |
| 6,234,968 B1 | 5/2001 | Sumanaweera et al. | |
| 6,468,213 B1 | 10/2002 | Knell et al. | |
| 6,569,102 B2 | 5/2003 | Imran et al. | |
| 6,618,206 B2 | 9/2003 | Tarakci et al. | |
| 6,663,567 B2 | 12/2003 | Ji et al. | |
| 6,685,645 B1 | 2/2004 | McLaughlin et al. | |
| 6,733,455 B2 | 5/2004 | Mo et al. | |
| 6,773,399 B2 | 8/2004 | Xi et al. | |
| 6,866,631 B2 | 3/2005 | McLaughlin et al. | |
| 6,866,632 B1 | 3/2005 | Chou et al. | |
| 2002/0028994 A1 | 3/2002 | Kamiyama | |
| 2002/0095087 A1 | 7/2002 | Mourad et al. | |
| 2003/0028113 A1 | 2/2003 | Gilbert et al. | |
| 2004/0006271 A1 | 1/2004 | Golland et al. | |
| 2004/0024316 A1 | 2/2004 | Xi et al. | |
| 2004/0064044 A1 | 4/2004 | Brock-Fisher | |
| 2004/0179332 A1 | 9/2004 | Smith et al. | |
| 2005/0049494 A1 | 3/2005 | Gritzky et al. | |

FOREIGN PATENT DOCUMENTS

| | | |
|---|---|---|
| JP | 58-157453 A | 9/1983 |
| WO | 00/31634 A1 | 6/2000 |
| WO | 03/093863 A1 | 11/2003 |
| WO | 2006/113445 A1 | 10/2006 |

OTHER PUBLICATIONS

Bushberg et al., "The Essential Physics of Medical Imaging," 2$^{nd}$ Ed., Lippincott Williams & Wilkins, Philadelphia, PA., pp. 509-510.

Ito et al., "Cho-onpa Shindan Sochi (Ultrasonograph)," PA07-547 *Corona Publishing Co. LTD.*,79-97, Aug. 26, 2002, 26 pages. (with English Translation).

Taylor et al., "Three dimensional sonoelastography: principles and practices," *Phys Med Biol* 45:1477-1494, 2000.

Zong et al., "Speckle Reduction and Contract Enhancement of Echocardiograms via Multiscale Nonlinear Processing," *IEEE Transactions on Medical Imaging* 17(4):532-540, Aug. 1998.

SOFTWARE-BASED SYSTEM ARCHITECTURE

MATLAB SIMULATION OF PIXEL-ORIENTED PROCESSING METHOD

PERSPECTIVE VIEW OF ZOOMED REGION OF FIG. 6, WITH IMAGE POINTS AT 1/2 WAVELENGTH SPACING

EFFECTS OF SIGNAL AVERAGING ON BAND-LIMITED NOISE ADDED TO RF DATA

SPATIALLY COMPOUNDED IMAGE RECONSTRUCTION USING UNIFORM ILLUMINATION METHOD

PERSPECTIVE VIEW OF ZOOMED REGION OF FIG. 8

ULTRASOUND IMAGING SYSTEM WITH PIXEL ORIENTED PROCESSING

BACKGROUND OF THE INVENTION

Field of the Invention

The present invention is directed to an ultrasound imaging architecture and, more particularly, to a system and method of capturing and processing ultrasound data and generating images therefrom utilizing pixel oriented processing techniques.

Description of the Related Art

Ultrasound Imaging has developed into an effective tool for diagnosing a wide variety of disease states and conditions. The market for ultrasound equipment has seen steady growth over the years, fueled by improvements in image quality and the capability to differentiate various types of tissue. Unfortunately, there are still many applications for ultrasound systems where the equipment costs are too high for significant adoption. Examples are application areas such as breast cancer detection, prostate imaging, musculoskeletal imaging, and interventional radiology. In these areas and others, the diagnostic efficacy of ultrasound imaging depends on excellent spatial and contrast resolution for differentiation and identification of various tissue types. These performance capabilities are found only on the more expensive ultrasound systems, which have more extensive processing capabilities.

Ultrasound imaging has always required extensive signal and image processing methods, especially for array systems employing as many as 128 or more transducer elements, each with unique signal processing requirements. The last decade has seen a transition to the improved accuracy and flexibility of digital signal processing in almost all systems except for those at the lowest tiers of the market. This transition has the potential for reducing system costs in the long term, by utilizing highly integrated digital circuitry. Unfortunately, the low manufacturing volumes of ultrasound systems results in substantial overhead and fixed costs for these unique circuits, and thus the transition to digital signal processing has not significantly reduced system cost.

While ultrasound systems have increasingly adopting digital processing technology, their architectures have not changed significantly from their analog counterparts. Almost all current systems on the market use a modular "flow-through" architecture, with signals and data flowing from one module to the next, as shown in FIGS. 1A and 1B. This is a natural method of dealing with the considerable complexity of ultrasound image formation and processing, and allows separate development teams to work somewhat independently on individual modules. FIG. 1A shows the three types of information processing that are typically performed with ultrasound systems—echo image processing, for normal 2D imaging; Doppler processing, for blood velocity measurements; and color flow image processing, for real-time imaging of blood flow.

A major disadvantage of the flow-through architecture is that each module must wait on its input data from the previous module before it can perform its own processing. The module must then deliver its result to the next module. Even within the blocks shown in FIG. 1A, there are many individual processing steps that are performed in series. Since the rate of system processing is determined by the rate of slowest processing function in the chain, all processing blocks must perform at high speed with minimal latencies, so as to not to introduce delays in seeing an image appear on the display as the scanhead is moved.

Another disadvantage of the flow-through architecture is that it makes inefficient use of resources. Most ultrasound exams are performed primarily with 2D echo imaging only, with only occasional use of Doppler blood velocity measurements or color flow imaging. This means that the complex and expensive hardware processing modules needed to perform these functions are sitting idle most of the time, as they cannot be used in other tasks.

BRIEF SUMMARY OF THE INVENTION

The disclosed embodiments of the present invention are directed to an ultrasound imaging method and system that performs all signal processing and image formation in software executing on commercial CPUs. The only custom hardware required in this approach is for transmission of acoustic pulses and data acquisition and signal conditioning of the received signals from the transducer. To accomplish this goal requires fundamental changes in the processing architecture of the ultrasound system to reduce the number of processing steps required in forming the image and to eliminate system latencies. It also requires maximum utilization of the processing resources of the CPU to achieve the processing throughput desired. As an important benefit, the new architecture allows improvements in system dynamic range that open up the possibility of utilizing new transducer materials in a low-cost scanhead design. In addition, new modes of acquisition are possible that may provide significant new diagnostic information.

The disclosed software-based ultrasound system architecture leverages the high volume, low cost processing technology from the computer industry by basing the design around a commercial computer motherboard. While some current ultrasound systems incorporate computer motherboards in their design, the computer is used only for the user interface and some system control and does not participate in any real-time processing tasks. In the disclosed architecture, the computer motherboard replaces almost all existing hardware, rather than complementing it. Basing the system in software on a general-purpose platform provides a flexible, high-performance imaging system at the lowest possible system cost. No custom integrated circuits are required for this approach, reducing system complexity and time-to-market. Moreover, as further improvements in CPU processing power are realized by the computer industry, they can be easily adopted by the system to enhance imaging performance or provide new modes of operation and information extraction.

The successful realization of the software-based ultrasound architecture represents a market breakthrough in the cost/performance ratio of ultrasound systems. Presumably, this can significantly increase the utilization of ultrasound in cost-sensitive applications that demand high image resolution and tissue differentiation for diagnostic efficacy. In addition, the low system cost and processing flexibility should open up new specialty application areas where ultrasound has not previously played a significant role.

In accordance with one embodiment of the invention, an ultrasound processing method is provided that includes generating an acoustic signal, receiving at least one echo of the acoustic signal at a plurality of receiving elements and obtaining an echo signal therefrom, storing each echo signal from each of the plurality of receiving elements, mapping a given pixel into a region of the stored echo signals, organizing the mapped region of the stored echo signals into an array for the given pixels, processing the array to generate a signal response for the given pixels, and using the signal response to obtain acoustic information for the given pixel.

In accordance with another aspect of the foregoing embodiment, an initial step is provided that includes generating a set of given pixels chosen to represent an area in a field of view of the transducer generating the acoustic signal, in which even given pixel in the array set has a known spatial relationship to the plurality of receiving elements. Preferably the method also includes generating an image from the acoustic information for the given pixels in the array.

In accordance with another aspect of the foregoing embodiment, the acoustic information can be used for one or more of the following, including, but not limited to, measuring and displaying spatial data, measuring and displaying temporal data, measuring and displaying blood flow data, and measuring and displaying tissue displacement responsive to induced mechanical displacement caused by an acoustic signal or acoustic transmit wave.

In accordance with another aspect of the foregoing embodiment, the method includes generating a plurality of acoustic signals, receiving echoes from the plurality of acoustic signals, and combining the received echoes over multiple generating and receiving cycles to enhance acoustic information obtained therefrom.

In accordance with another aspect of the foregoing embodiment, the stored echo signals are combined and averaged. Furthermore, the signal response comprises an average of the stored echo signals.

In accordance with another aspect of the foregoing embodiment, the method includes combining results of multiple processing of the array to derive enhanced acoustic information.

In accordance with another aspect of the foregoing embodiment, the enhanced acoustic information includes spatial compounding that improves contrast resolution of a final image generated therefrom. In addition, the combined signals are representative of Doppler information associated with moving tissue or moving blood cells.

In accordance with another aspect of the foregoing embodiment, the receiving, obtaining, and storing of echo signals is done at a rate that is higher than a rate of processing the array.

In accordance with another embodiment of the invention, an ultrasound processing method is provided that includes generating an acoustic signal, receiving at least one echo of the acoustic signal at a plurality of receiving elements and obtaining an echo signal therefrom, storing each echo signal from each of the plurality of receiving elements, mapping a given voxel into a region of the stored echo signals, organizing the mapped region of the stored echo signals into an array for the given voxel, processing the array to generate a signal response for the given voxel, and using the signal response to obtain three-dimensional acoustic information for the given voxel.

In accordance with another aspect of the foregoing embodiment, all of the features of the first embodiment described above are applicable to this second embodiment of the invention.

In accordance with another embodiment of the invention, a method of processing acoustic echoes is provided that includes storing acoustic echo signals received from a plurality of receiving elements, mapping a given pixel into a region of the stored echo signals, organizing the mapped region of the stored echo signals into an array for the given pixel, performing operations on the array to generate a signal response for the given pixel, and using the signal response to obtain acoustic information for the given pixel.

In accordance with another embodiment of the invention, an ultrasound processing system is provided that includes a module adapted to generate an acoustic signal, receive at least one echo of the acoustic signal at a plurality of receiving elements in the module and obtain a plurality of echo signals therefrom, and means for processing that communicates with the module and is adapted to map a given pixel into a region of stored echo signals received from the module, to organize the mapped region of the stored echo signals into an array for the given pixel, to perform operations on the array to generate a signal response for the given pixel, and to use the signal response to obtain acoustic information for the given pixel.

In accordance with another aspect of the foregoing embodiment, the processing means is adapted to initially generate a set of given pixels in which each given pixel in the set has a known spatial relationship to a receiving element in the module. Ideally, the processing means is configured to generate an image from the acoustic information for the given pixels in the array. Alternatively or in combination therewith, a means for displaying an image is provided that receives the signal response from the processing means for generating an image on a computer display or in printed form or in other forms known to those skilled in the art.

In accordance with another embodiment of the present invention, an ultrasound processing system is provided that includes a module adapted to generate an acoustic signal, receive at least one echo of the acoustic signal at a plurality of receiving elements in the module and obtain a plurality of echo signals therefrom, and means for processing that communicates with the module and is adapted to map a given voxel into a region of stored echo signals received from the module, to organize the mapped region of the stored echo signals into an array for the given voxel, to perform operations on the array to generate a signal response for the given voxel, and to use the signal response to obtain acoustic information for the given voxel.

In accordance with another aspect of the foregoing embodiment of the invention, multiple 2D images planes are displayed as arbitrary slices of the real-time 3D data set.

In accordance with another aspect of the foregoing embodiment of the invention, multiple 2D arbitrary image plane slices and a 3D rendering are displayed in real time.

As will be readily appreciated from the foregoing, the benefits of changing to a software-based ultrasound system architecture implemented on commercially available computing platforms include:

Significantly lower cost of hardware.

Lower development costs and faster time to market by avoiding lengthy design cycles for custom integrated circuits (ASICs).

Direct leveraging of cost/performance advances in computer technology.

Flexibility for development of many new processing approaches, in commercial and academic environments.

Increased diagnostic capability, based on image quality improvements, for cost sensitive application areas.

Increased utilization of ultrasound in specialty applications where cost has been a barrier to adoption.

BRIEF DESCRIPTION OF THE DRAWINGS

The foregoing and other features and advantages of the present invention will be more readily appreciated as the same become better understood from the following detailed description of the present invention when taken in conjunction with the following drawings, wherein.

DETAILED DESCRIPTION OF THE INVENTION

Figure 1A:
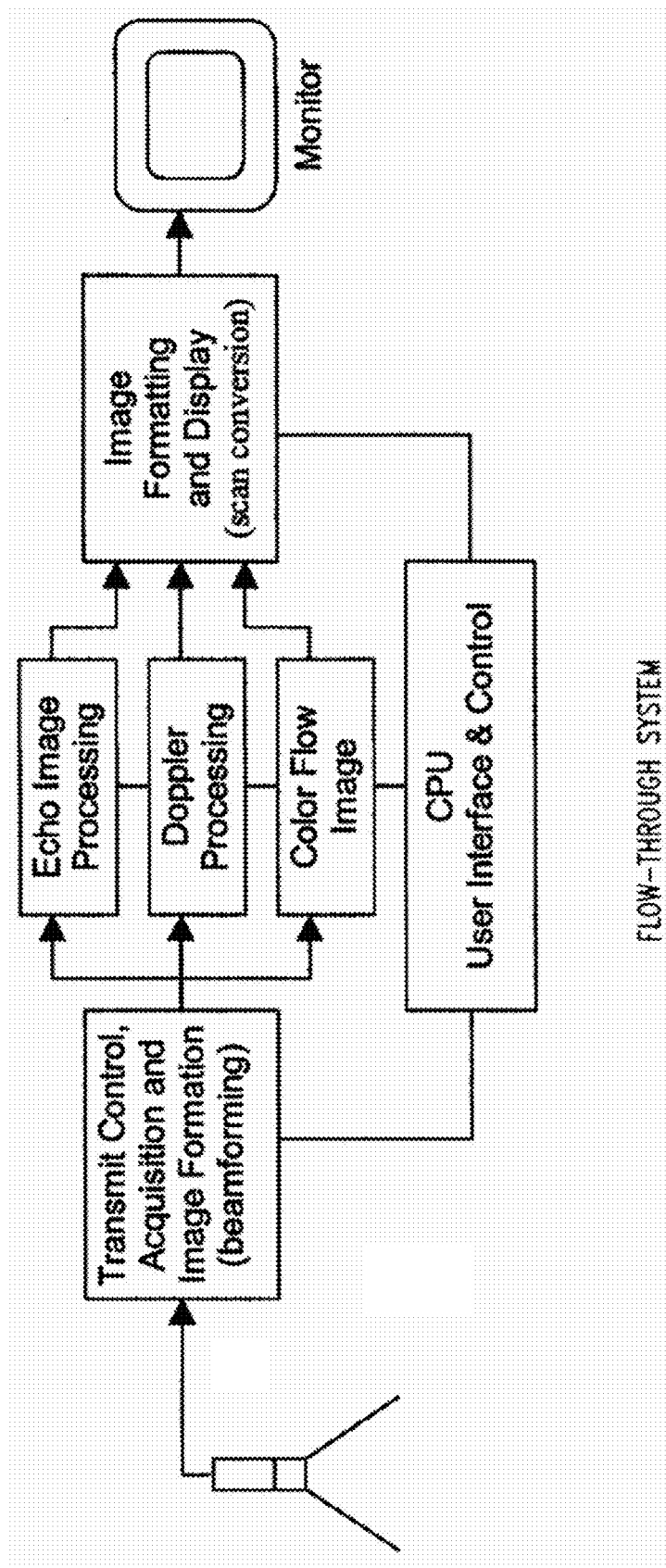
FIGS. 1A and 1B are schematic representations of a known flow-through ultrasound image formation architecture.
Figure 1B:
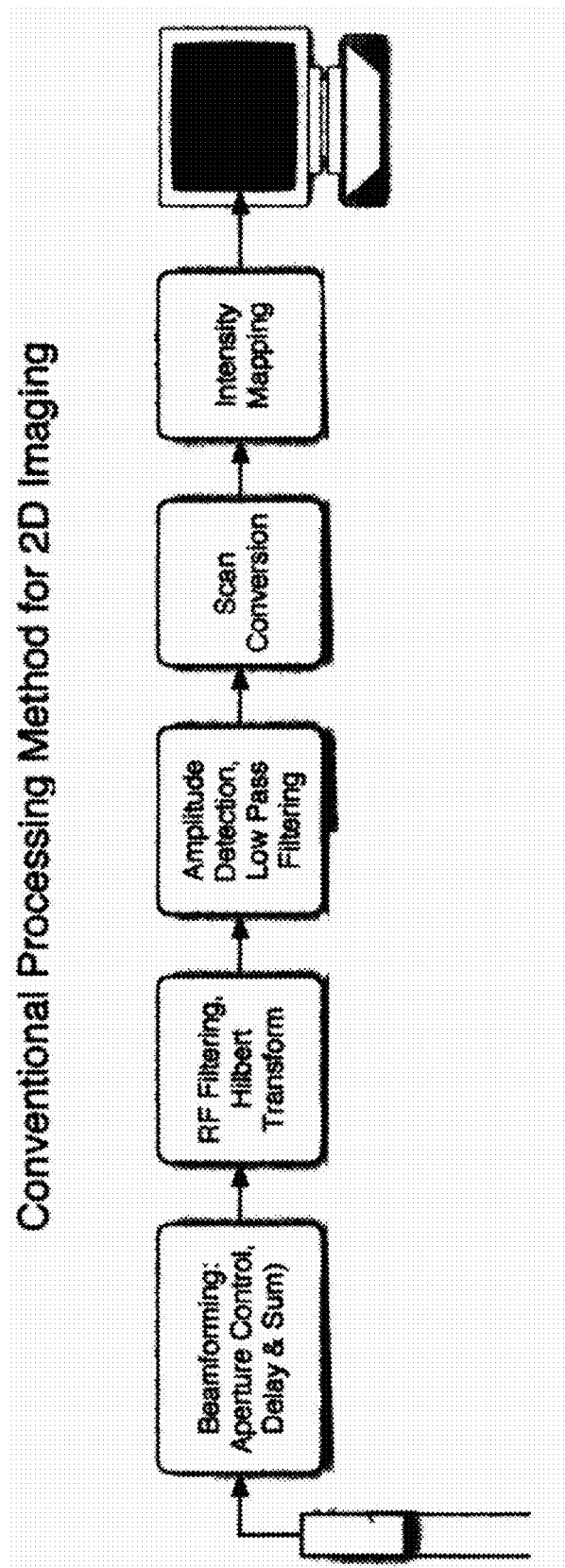
Figure 2:
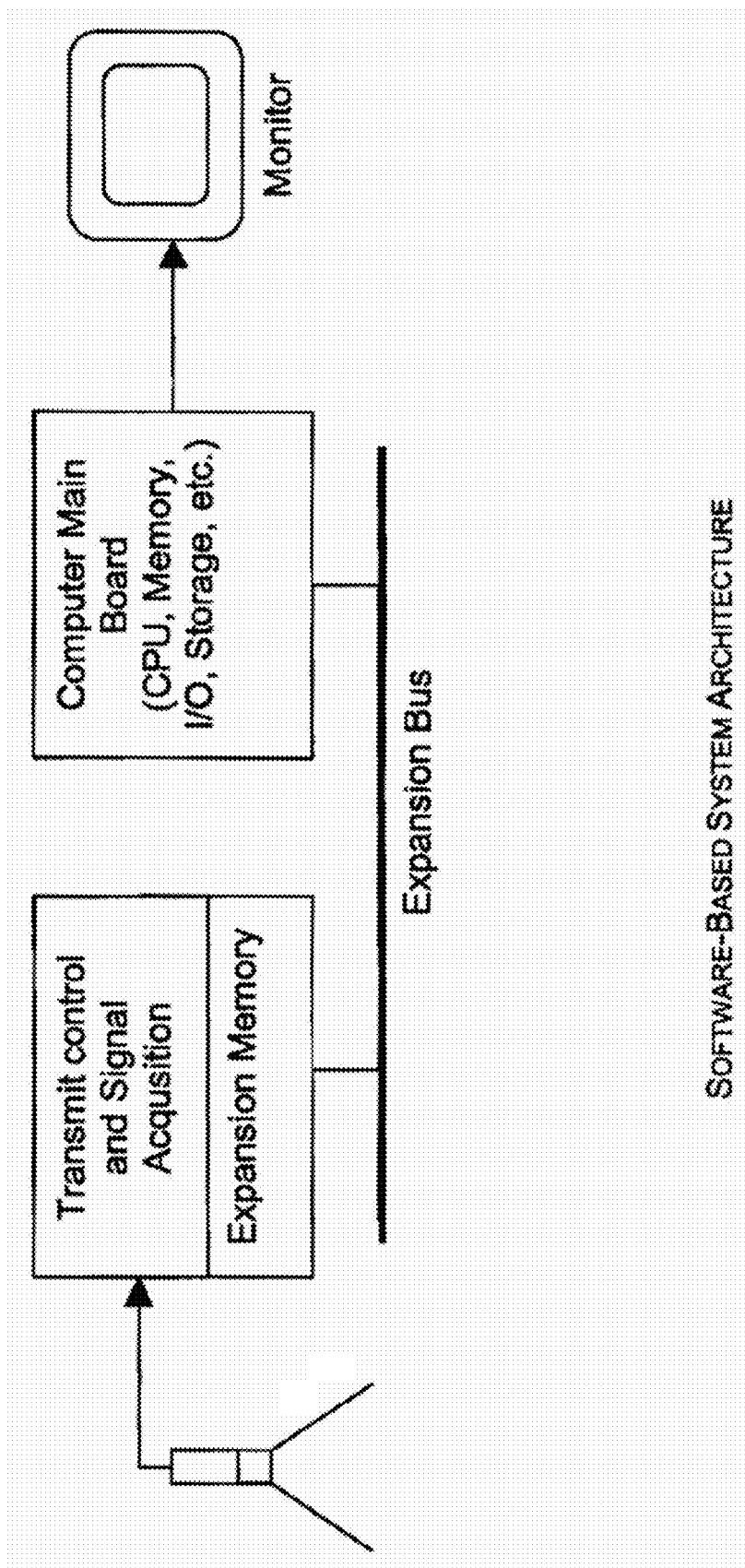
FIG. 2 is a schematic representation of a software-based architecture of one embodiment of the present invention.

The software-based method and system architecture in accordance with one embodiment of the invention implements all real-time processing functions in software. The proposed architecture is shown schematically in FIG. 2.

The only custom hardware component in the software-based system is a plug-in module to the expansion bus of the computer that contains the pulse generation and signal acquisition circuitry, and a large block of expansion memory that is used to store signal data. The signal acquisition process consists of amplifying and digitizing the signals returned from each of the transducer elements following a transmit pulse. Typically, the only filtering of the signals prior to digitization, other than the natural band-pass filtering provided by the transducer itself, is low pass, anti-aliasing filtering for A/D conversion. The signals are sampled at a constant rate consistent with the frequencies involved, and the digitized data are stored in memory with minimal processing. The straight-forward design of the signal acquisition allows the circuitry to be implemented with off-the-shelf components in a relatively small amount of board area.

Figure 3:
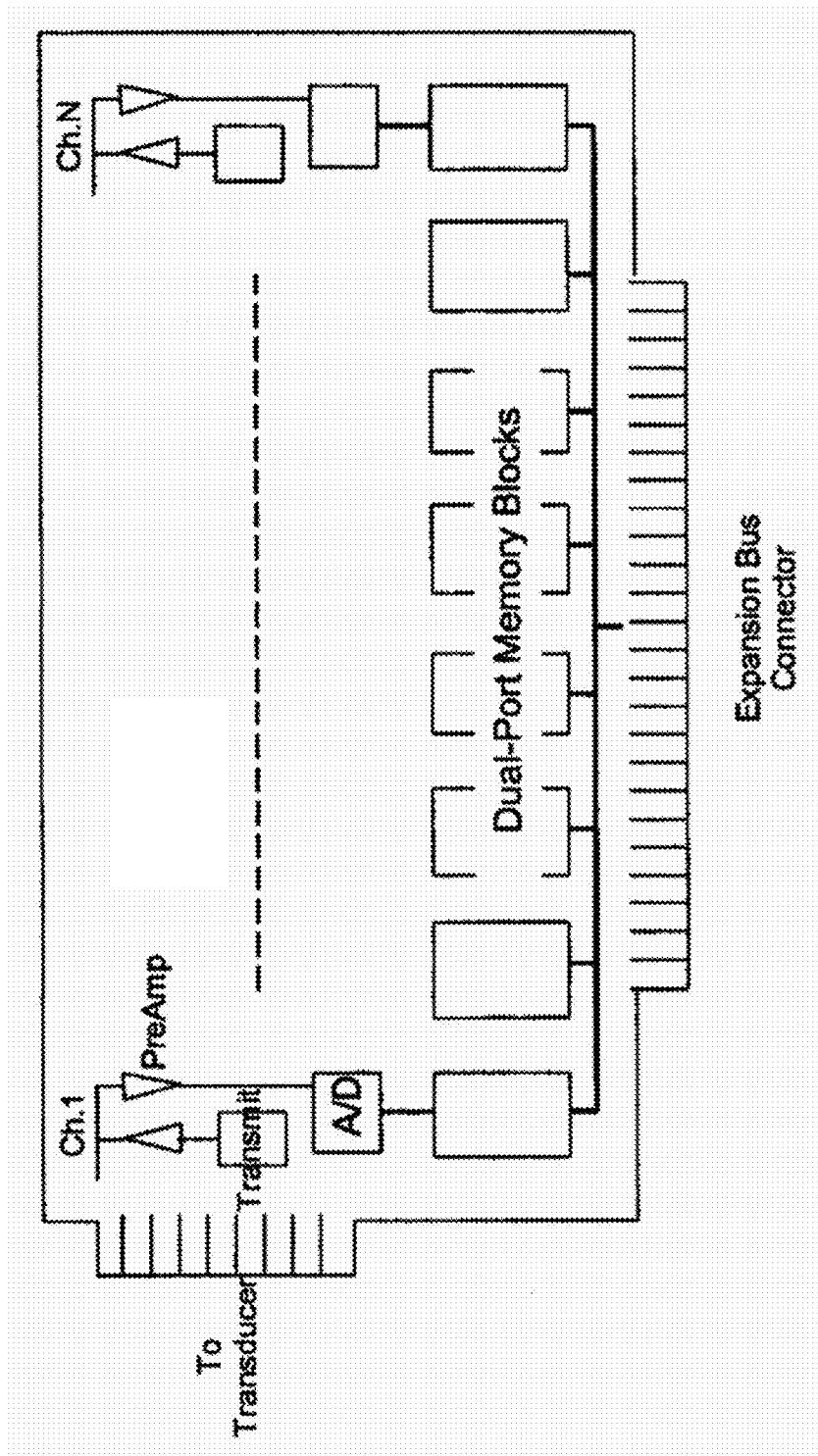
FIG. 3 is a diagram of a plug-in module formed in accordance with one embodiment of the present invention.

A more detailed look at the plug-in module is shown in FIG. 3. Multiple acquisition channels are shown, each composed of a transmitter, receiver pre-amplifier, A/D converter, and memory block. During receive, the transducer signals are digitized and written directly to the individual memory blocks. The memory blocks are dual-ported, meaning they can be read from the computer side at the same time acquisition data is being written from the A/D converter side. The memory blocks appear as normal expansion memory to the system CPU(s). It should be noted that the size of the plug-in module is not limited to the normal size of a standard computer expansion card, since the system is preferably housed in a custom enclosure. Also, multiple plug-in modules can be used to accommodate a large number of transducer elements, with each module processing a subset of the transducer aperture.

The components for the plug-in module, including amplifiers, A/D converters and associated interface circuitry, and the needed components for transmit pulse generation and signal acquisition are readily commercially available components and will not be described in detail herein. The memory block needed for RF data storage of echo signals obtained from received echoes is essentially the same circuitry as found in commercially available plug-in expansion memory cards, with the addition of a second direct memory access port for writing the digitized signal data. (The received echo signal data is generally referred to as RF data, since it consists of high frequency electrical oscillations generated by the transducer.) The memory is mapped into the central processor's address space and can be accessed in a manner similar to other CPU memory located on the computer motherboard. The size of the memory is such that it can accommodate the individual channel receive data for up to 256 or more separate transmit/receive cycles. Since the maximum practical depth of penetration for round trip travel of an ultrasound pulse in the body is about 500 wavelengths, a typical sampling rate of four times the center frequency will require storage of as many as 4000 samples from an individual transducer element. For a sampling accuracy of 16 bits and 128 transducer channels, a maximum depth receive data acquisition will require approximately one megabyte of storage for each transmit/receive event. To store 256 events will therefore require 256 MB of storage, and all totaled, a 128 channel system could be built on a few plug-in cards.

Another aspect of the software-based ultrasound system is the computer motherboard and its associated components. The motherboard for the proposed design should preferably support a multi-processor CPU configuration, for obtaining the needed processing power. A complete multi-processor computer system, complete with power supply, memory, hard disk storage, DVD/CD-RW drive, and monitor is well-known to those skilled in the art, can be readily commercially purchased, and will not be described in greater detail.

A software-based ultrasound system must truly achieve "high-performance," meaning image quality comparable to existing high-end systems, in order to provide a significant benefit to the health care industry. This level of performance cannot be achieved by simply converting the flow-through processing methods of current systems to software implementations, since a simple addition of all the processing operations needed for one second of real-time imaging in the flow-through architecture gives a number that exceeds the typical number of operations per second currently achievable with several general purpose processors. Consequently, new processing methods are required that achieve a much greater efficiency than the flow-through methods.

Figure 4:
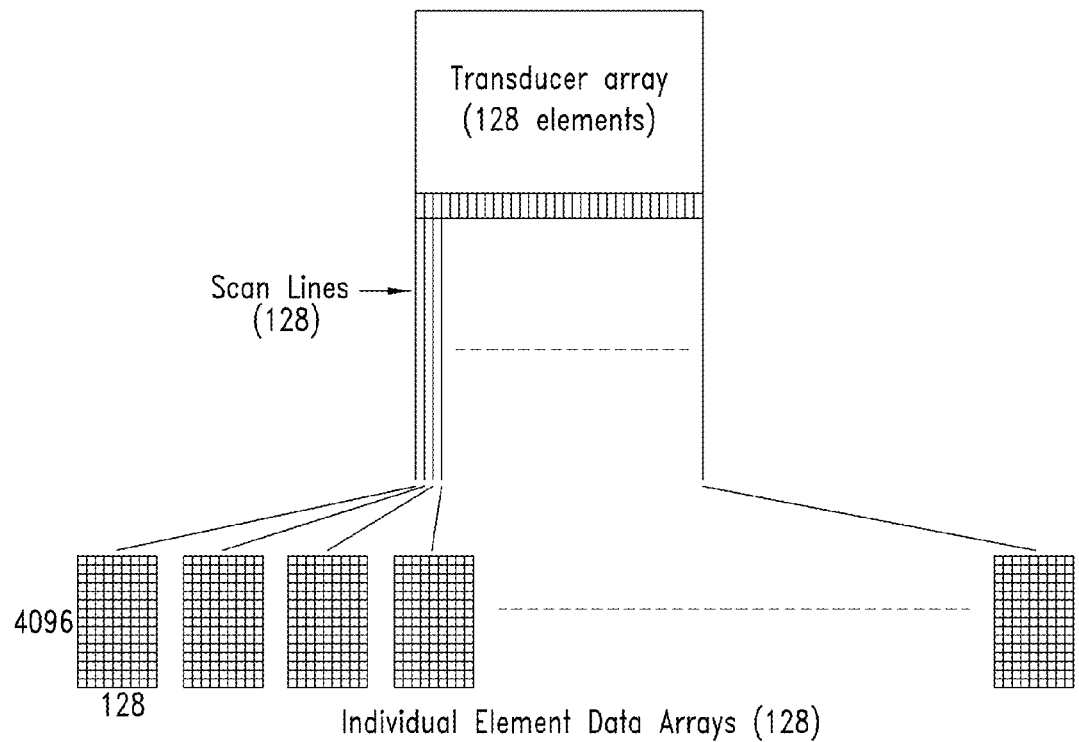
FIG. 4 is a schematic representation of the acquisition data for a 128 element linear array formed in accordance with the present invention.

In one embodiment of the software-based ultrasound system architecture of the present invention, the input data for signal and image processing consists of the set of RF samples acquired from individual transducer channels following one or more transmit events. For an example, let us consider a typical 2D imaging scanning mode with a 128 element linear transducer array, as shown in FIG. 4.

In this case, a 'transmit event' would consist of timed pulses from multiple transducer elements to generate a plurality of acoustic waves that combine in the media to form a focused ultrasound beam that emanates outwards from an origin point on the transducer at a specific element location. Multiple transmit events (128 in all) produce ultrasound beams that are sequentially emitted incrementally across the width of the transducer face, thus interrogating an entire image frame. For each of these transmit beams, the received echo data are collected from each of the 128 receiver elements in the transducer and organized into a data array with each column representing the sampled echo signal received by the corresponding transducer element. Thus, each array has 128 columns, corresponding to the 128 transducer elements, and a number of rows corresponding to the number of samples in depth that were taken (in this case, we will assume 4096 rows resulting in 4096 samples). These 128 data arrays then constitute an RF data set that is sufficient to produce one complete image frame.

It is worth noting that in the flow-through architecture, the RF data set described above does not even exist (at least not all at one time), since the beam and image formation takes place as the data streams in from the transducer. In other words, as the data return to each element after a transmit event, they are processed and combined (referred to as beamforming) to generate a single RF signal representing the focused return along a single beam (scanline). This RF signal is processed (again in real-time) into echo amplitude samples, which are stored in a memory array. When all beam directions have been processed, the echo amplitude data are then interpolated and formatted into a pixel image for display. Since all processing takes place in real-time, the processing circuitry must be able to 'keep up' with the data streaming in from the transducer elements.

In the software-based architecture of the present invention, all input data is stored prior to processing. This uncouples the acquisition rate from the processing rate, allowing the processing time to be longer than the acquisition time, if needed. This is a distinct advantage in high frequency scans, where the depth of acquisition is short and the sample rate high. For example, a 10 MHz scanhead might have a useable depth of imaging of around four centimeters. In this case, the speed of sound in tissue dictates that each of the 128 transmit/receive events acquire and store their data in 52 microseconds, a very high acquisition data rate. In the flow-through architecture, these acquisition data would be formed into scanlines in real-time at high processing rates. In the software-based architecture of the present invention, the storage of RF data allows the processing to take as long as the frame period of the display, which for real-time visualization of tissue movement is typically 33 milliseconds (30 frames/second). For 128 pixel columns (the rough analogy to scan lines), this would allow 258 microseconds of processing time per column, rather than the 52 microseconds of the flow-through architecture. This storage strategy has the effect of substantially lowering the maximum rate of processing compared with the flow-through architecture for typical scan depths.

Pixel-Oriented Processing

The storing of input data reduces the maximum processing rates but doesn't necessarily reduce the number of processing steps. To accomplish this, a new approach to ultrasound data processing is taken. The first step is to recognize that the ultimate goal of the system when in an imaging mode is to produce an image on the output display. An ultrasound image has a fundamental resolution that depends on the physical parameters of the acquisition system, such as the frequency and array dimensions, and can be represented as a rectangular array of pixel values that encode echo amplitude or some other tissue (acoustic) property. The density of this rectangular pixel array must provide adequate spatial sampling of the image resolution. It is recognized that display images need not consist only of rectangular arrays of pixels, but could consist of any arbitrary set of pixels, representing different geometric shapes. The next step is to start with one of the pixels in this image array and consider which sample points in the RF data set contribute to the calculation of this pixel's intensity, and determine the most efficient way of accessing and processing them. This approach is a completely different approach than the one utilized by the current flow-through architecture because only information that contributes to pixels on the display needs to be processed. In the approach of the present invention, a small region on the display image will take less overall processing time than a large image region, because the small region contains fewer pixels. In contrast, the flow-through processing methods must be designed to handle the maximum data stream bandwidths, independent of the image region size.

After processing the pixel array required to adequately represent the ultrasound image, the array can be rendered to the computer display at an appropriate size for viewing. The graphics processor of the computer, requiring no additional CPU processing, can typically carry out this operation, which consists of simple scaling and interpolation.

Figure 5:
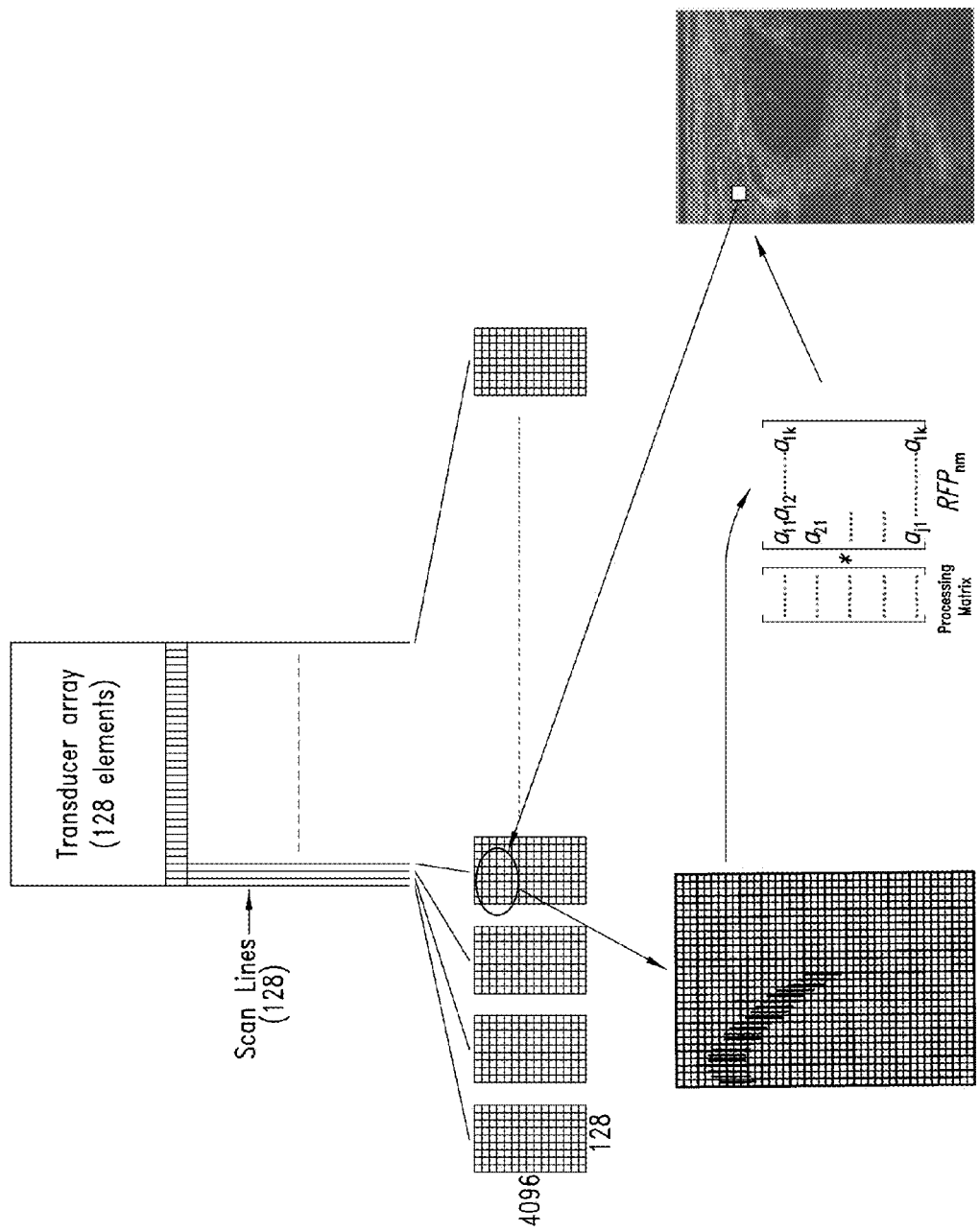
FIG. 5 is an illustration of a pixel mapping process of the present invention.

We next consider the processing strategy for a single pixel of our ultrasound image. In this discussion, we will assume that our objective is to obtain the echo intensity at the corresponding spatial location of the pixel with respect to the transducer array. Other acoustic parameters may be similarly obtained. Our first step is to find the region of acquisition RF data containing samples that contribute to the echo intensity calculation. To accomplish this for the scanning method of FIG. 4, we first find the acquisition scan line that comes closest to intersecting the pixel location, and then use the corresponding individual element data array. FIG. 5 shows this mapping process for an example pixel in an ultrasound image. In FIG. 5, the indicated pixel maps to the closest acquisition line of the scan, which in this case is scan line 4, whose RF data resides in the fourth individual element RF data array (which represents data collected from the fourth transmit/receive event). More than one RF data array could be chosen as contributing to the pixel signal, but for this example we will consider only a single data array.

Out next step is to map out the region in the individual element array containing samples that contribute to the pixel's intensity calculation. This mapping process is fairly complex and depends on several factors. The transducer elements each have a region of sensitivity that determines how they will respond to a signal returning from a particular point in the image field. For a given image point, only elements that have sensitivities above a predetermined threshold need be considered, since if the sensitivity is too low, an element will not contribute useful information to the pixel's quantity. This sensitivity threshold then determines the number of element data columns to include in the mapped region. As shown in FIG. 5, elements on the far right hand side of the transducer are not included in the mapped data region.

The starting depth of the mapped data region is determined by the arrival time of the returning echo at each individual transducer element. As shown in FIG. 5, the image point signal for elements further away from the image point is captured later in time, and so the starting point of the data set is deeper in memory. Finally, the depth range needed for the mapped data region is dependent on the duration of the transmit pulse generated. Longer transmit pulses will excite the image point for a longer period of time, generating echo signals that extend over a larger depth span of the RF memory.

Fortunately, many of the factors that go into determining the region of mapped data can be pre-computed for a given pixel grid, since this grid does not change over the multiple frames of a real-time image sequence. Using pre-computed factors, the mapped data region for a given pixel can be rapidly and efficiently determined, saving considerable computations during real-time imaging.

After selecting out the pixel mapped RF data, we can organize it into a matrix, $RFP_{nm}$, as shown below.

$$RFP_{nm} = \begin{bmatrix} a_{11} a_{12} \ldots a_{1k} \\ a_{21} \\ \ldots \\ \ldots \\ a_{j1} \ldots a_{jk} \end{bmatrix}$$

The notation '$P_{nm}$' refers to the image pixel in row n, column m. The matrix columns are the vertical bars of FIG. 5 where it is assumed that the number of samples, j, in each vertical bar are the same. The number of samples, j, is dependent on the range of RF data in time needed for capturing the signal generated by the transmit pulse. The index, k, is the number of channels in the RF data array that have adequate signal strength from to the image point to participate in the intensity calculation.

The process of computing the signal intensity value of pixel $P_{nm}$ now consists of a series of matrix operations that eventually lead to a single value. When the computations are organized in this fashion, it quickly becomes apparent that some of the matrix operations may be algebraically combined, leading to fewer computational operations. Without going into specific details, the operations of sample interpolation to find the correct delay values for individual elements, bandpass filtering, Hilbert transform filtering for quadrature detection, and final summation can be performed in a single matrix multiply, then taking the trace of the resulting matrix (The trace of a matrix is the sum of the elements along the main diagonal. Since only the main diagonal of the result of the matrix multiply is needed, the multiply operation can be considerably simplified). Since many of the matrices needed for these operations are independent of the pixel location, they can be pre-computed prior to real-time operation. The processing matrix can then be formed by combining pre-computed elements with elements that change dynamically with the pixel location (such as interpolation parameters). With a fixed number of interpolation steps, it is even possible to select the rows of the processing matrix from a collection of pre-computed vectors. The use of pre-computed data for forming the processing matrix, while not essential to the method, can substantially reduced processing time for real-time operation.

The signal value derived from the pixel oriented processing is typically a complex signal value, which can be represented by quadrature samples I, and Q. To obtain the echo intensity at our image point, the magnitude of the signal is computed, using a simple square root of the sum of the squares of the quadrature samples. If phase information is needed (as for additional processing for Doppler sensing), the complex signal representation can be retained.

With this computational approach, the number of processing steps required to compute a pixel's reconstructed signal value are reduced substantially over the flow-through architecture. Estimates derived from sample calculations indicate that for typical image sizes, operation reductions as great 10-to-1, a full order of magnitude, are possible. Moreover, the matrix operations needed can be carried out using the vector processing capabilities of modern processors, where multiple data can be operated on using single instructions (These instructions are called 'SIMD' instructions, which stands for 'single instruction, multiple data.' For example, the Altivec processing unit of the PowerPC can perform a multiply and accumulate on two vectors, containing eight 16-bit samples each, in a single clock cycle). These factors make it feasible to perform real-time processing of ultrasound image data using one or more general-purpose processors.

It is important to note that for the typical imaging scan, the pixel oriented processing method generates no intermediate data sets—the processing method goes directly from unprocessed acquired RF data to pixel intensity, through a series of matrix operations on the mapped acquisition data. Each pixel of the output image maps to its own unique region of the acquisition data, and has its own processing matrix, allowing a direct conversion from raw acquisition data to the desired acoustic signal estimate. This is not the case with the traditional flow-through architecture, which typically processes the individual channel RF data to beamformed RF samples along transmit/receive ray lines and then generates a detected amplitude data set that is then scan converted for display. In the pixel-oriented processing method, even the process of scan-conversion, which for a sector format scan involves polar-to-rectangular coordinate conversion, is included in the single processing operation.

For irregular shapes of image data, it is more appropriate to consider the collection of pixels to be rendered as a pixel set. The actual display presented to the user can then consist of multiple pixel sets processed and rendered as a display frame. This concept is useful for implementing complex scan formats, as well as the various standard modes of ultrasound scanning, such as 2D imaging combined with Doppler imaging, 2D imaging combined with time-motion imaging (M-mode), or 2D imaging combined with spectral Doppler display. In the case of time-motion imaging and spectral Doppler, the pixel set might consist of a single pixel column, which is moved sequentially across the display.

It should also be noted that the pixel-oriented processing method generates image data that can be precisely measured on the display to derive other types of empirical data. In 2D imaging, each pixel has a known spatial relationship to the transducer, consequently, a measurement distance in pixels can be easily converted to a measurement distance in the media being imaged.

One possible impediment to the processing method described above is bus bandwidth. The memory arrays of received RF data associated with each transmit event must be accessed to compute image points and this access must occur over the expansion bus of the computer. If, for the case of a maximum range ultrasound acquisition, all samples in each memory array were needed for processing, the required bandwidth for the sampling method described above would be 128×4096×(2 bytes/sample)×(128 arrays)=128 MBytes per frame (The second level caching of accessed samples insures that samples needing multiple times for processing in a given frame will be assessed from the cache after the first access, rather than over the expansion bus). At 30 fps, this would amount to a rather large bandwidth of 3.75 GBytes/second, which is at the limits of the current capabilities of most computer buses (the PCI-Express bus is specified at a peak data rate of 256 KBytes/sec/lane, which for a 16 lane expansion slot provides 4 GBytes/sec of transfer capability). Fortunately, due to the factors explained above, only a subset of the samples in each memory array are needed to compute the image points. Since each transducer element has a limited spatial range of sensitivity, not all elements contribute to a given reconstruction point. Moreover, the typical round trip imaging range for most applications is around 500-600 wavelengths (for example, 8-10 cm for a 5 MHz transducer), so that the memory arrays are only partially filled. These factors result in a typical bus bandwidth requirement of around 1-2 GBytes for 30 fps imaging, which is well within the capabilities of current computer expansion buses.

A further reduction of bus bandwidth can be accomplished by using fewer transmit events, which amounts to a type of multi-line imaging—a technique that is commonly used on high-end ultrasound systems to improve frame rate. Since the transmit beam can be broadened to cover the width of the image field with fewer transmit/receive events, the number of individual element data arrays can be reduced. In this case, multiple pixels along a row fall within the beam pattern of a single transmit. These multiple pixels will still have their own mapped data region, but the regions will all be from the same data array, thus reducing the amount of data that must be transferred over the bus. The pixel-oriented processing method can easily accommodate this type of image acquisition and processing.

Figure 6:
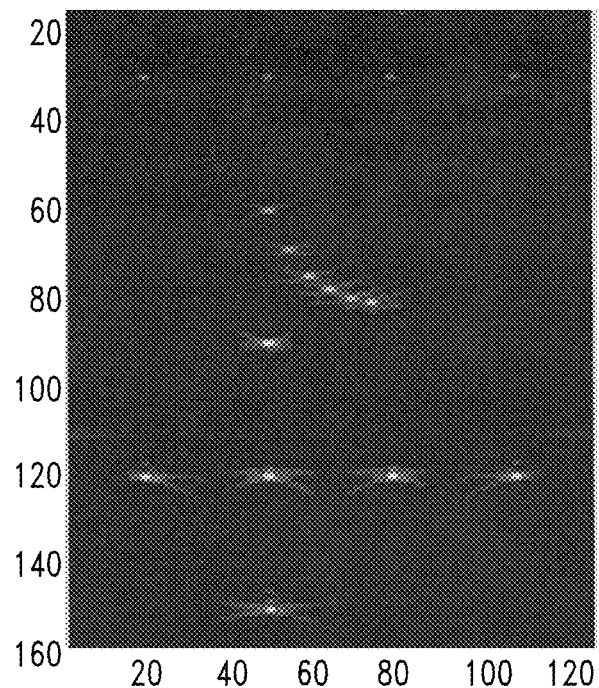
FIG. 6 is an image of target points obtained from a pixel-oriented simulation of the present invention.
Figure 7:
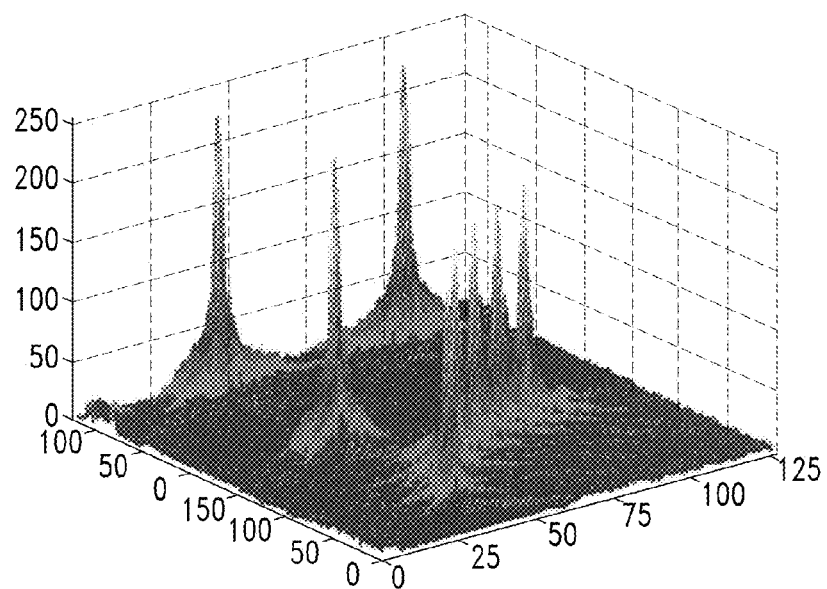
FIG. 7 is an isometric representation of the data from FIG. 6.

Simulation studies have been performed to address the image quality and computational speed of the pixel-oriented processing method. An image of simulated point targets arranged in a pattern is shown in FIGS. 6 and 7. The linear transducer array simulated is composed of 128 elements at 1 wavelength spacing. Since the simulation is in wavelength units, it is independent of the ultrasound center frequency. The transmit pulse used in this simulation is a cosine weighted three cycle burst, which is a fairly typical pulse shape for current transducers. The transmit focus is set at 100 wavelengths, and accounts for the increased intensity of the echo amplitudes around this range. The spacing of image points in the simulation is at one-wavelength intervals, which is adequate to represent the spatial resolution of this reconstruction. FIG. 7 shows a perspective view of a zoomed region of FIG. 6 (50 to 130 wavelengths in depth, 32 to 96 wavelengths laterally. The ability to reconstruct enhanced views of a sub-region of the image field is another strength of the pixel-oriented processing technique.

To generate larger image sizes for high-resolution displays, the ultrasound image can be interpolated to larger display sizes using the processing capability of the computer's graphic card, requiring no additional CPU processing. This process is illustrated by referring to the image in FIG. 6, which contains only 18560 image points, but has been interpolated to a much larger number of pixels (300 pixels per inch) for rendering on the page.

These simulation studies have verified both the accuracy and speed of the pixel-oriented processing method. It is important to note that all of the processing functions of an ultrasound imaging system have been implemented, including the complex process of beamforming. Further optimization of the processing algorithms can yield higher processing rates, allowing for more complex processing or the rendering of more pixels per image. In addition, the doubling of processor speed with every 18 months will provide a significant boost to pixel processing rates.

The software-based architecture of the present invention opens up the possibility of supporting transducers constructed with non-conventional materials and methods, such as low-cost plastic polymer transducers. It accomplishes this by completely de-coupling the acquisition process from the signal and image formation processing. With a minor change to the RF data storage memory interface, the memory writes can be changed to read-modify-writes, allowing input data to be summed with data already in memory. This change allows RF signals to be averaged over multiple identical transmit events, to reduce the effects of system noise and improve dynamic range. Averaging the RF signals permits significant SNR gains compared with averaging amplitude images.

Much of the noise in ultrasound systems is a result of thermal and radiated digital noise from the electronics of the system. The remaining noise is usually environmental RF noise, picked up by the transducer acting as an antenna. In both cases, the noise spectrum is fairly flat, so that with the system filtering of the RF signals, the noise appears as band-limited white noise. This noise typically determines the maximum gain that can be applied to an input signal and thus the penetration of the system, as the returning signals are attenuated as they travel increasing distances through the body.

Figure 8:
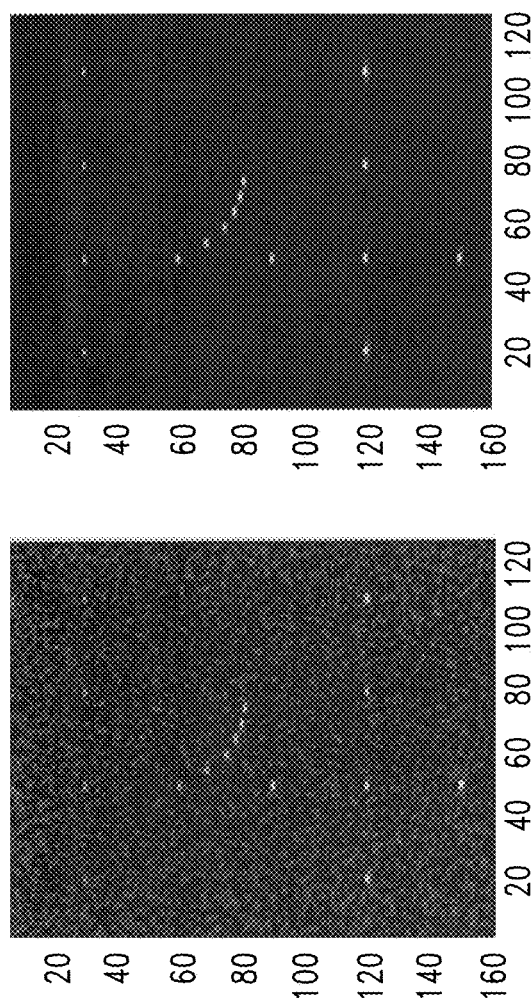
FIG. 8 is a side-by-side comparison of two images of target points obtained from a pixel-oriented simulation of the present invention.

As mentioned above, the use of signal averaging with the new system architecture can improve signal-to-noise and thus dynamic range significantly. For shallow depths, such as below four or five centimeters, it is feasible to use multiple transmit events for each ultrasound beam direction. The round trip travel time of a pulse traveling to a four centimeter depth is only 52 microseconds, allowing 16 transmit/receive cycles in 832 microseconds. Since movement in the body (with some exceptions) is typically below two or three cm/sec, an echo interface will only move by a small fraction of a wavelength (approximately $\frac{1}{16}$ wavelength at 5 MHz) in the time it takes to acquire the data for these 16 pulses. A full ultrasound frame using 128 beam positions would then take 106 milliseconds to acquire, giving a useable frame rate of 10 frames per second. This method of acquisition would be expected to result in a four times improvement in signal-to-noise, or about 12 dB. This improvement in signal-to-noise has been verified in simulation studies. FIG. 8 shows two simulated images processed using the pixel-oriented processing method. The image on the left is derived from RF data with one transmit pulse per beam, where band-limited white noise approximately 8 times the point target signal strength has been added in each channel. The image on the right uses the same signal to noise ratio for the RF data, but is derived from the average of 16 separate transmit/receive events per beam direction.

The implementation of signal averaging in the acquisition of transducer signals should result in sensitivity and penetration improvements no matter what transducer material is used. For example, it could facilitate the utilization of arrays made from micro-electromechanical silicone devices, which utilize tiny silicone drums to transmit acoustic information. Finally, for typical transducers made using PZT, it should also allow acoustic power levels to be reduced without sacrificing imaging performance in conventional exams.

Another benefit of low power, high dynamic range ultrasound imaging may be in the use of micro-bubble contrast agents to improve visualization of blood flow. Typical power levels result in the rapid destruction of the micro-bubbles, thus limiting visualization studies. Lower power levels should provide longer contrast lifetimes and may permit new clinical protocols.

The flexibility of the new software-based ultrasound architecture provides other advantages over the standard flow-through architecture. Previously, we have described how the new pixel-oriented processing methods can be used to implement standard ultrasound imaging acquisition modes. Since individual channel RF data are captured in memory, alternate modes of ultrasound imaging can also be supported. A significant example is often referred to as the 'uniform illumination imaging method,' or 'flash transmit method.' In this approach, the entire image field is interrogated at once with a single, unfocused transmit pulse, followed by acquisition of the returned echo signals from each individual element in the transducer array into a memory buffer. With suitable processing of the individual element data, an entire image plane can be reconstructed, without the need for further transmit pulses. The flash transmit technique can therefore acquire a full image in the same time it takes to acquire a single scan-line using the conventional method, providing theoretical frame rates as much as 128 times higher than a typical scan.

The human eye has a fairly slow response time, and as a result, there is not much benefit for ultrasound imaging display rates beyond around 30 frames per second. There are applications, however, such as pediatric cardiac imaging and analysis of heart valve motion, where it is desirable to have a much higher acquisition rate. To serve these applications, the flash transmit imaging technique can be used to acquire RF data frames, which can be stored in successive memory locations at a high acquisition rates in real-time. For real-time viewing, frames can be selected out of the acquisition stream at a lower rate for processing and display. When the scanning is stopped, all acquisition frames in memory can then be processed and played back at normal or reduced viewing rates, allowing full slow-motion analysis of the rapid tissue movement.

As one might expect, there are some disadvantages to the flash transmit imaging technique. Since the transmit pulse is unfocused, there will obviously be some loss in spatial resolution, although this loss will be confined to the lateral spatial dimension only. Also, since the transmit energy is more diffuse, there will be some loss of echo intensity. Finally, since the larger echo targets in the image are seen 'all the time,' instead of only along specific scan-lines, a high dynamic range reconstruction is required to prevent masking of the smaller echo signals. These deficits have typically led to rejection of the flash transmit reconstruction approach for normal imaging by ultrasound system designers.

The fact that the high frame rate capability of the flash transmit reconstruction technique can be leveraged to reduce or eliminate many of the above-mentioned deficits is often overlooked. In fact, the high frame rates possible with this approach open the door to substantial improvements in contrast resolution, tissue differentiation, and blood flow imaging that are not possible with the conventional image method. For example, recovery of lateral spatial resolution and substantial improvements in contrast resolution can be obtained using spatial compounding with the flash transmit method. The unfocused transmit pulse can be steered through multiple angles to interrogate the media targets from several directions in a time period short enough not to introduce motion artifacts. The images from the individual steering angles are then combined to produce a composite image. Even using as many as nine different angles requires only nine transmit pulses, which for a 10 cm image depth example takes only 1.2 milliseconds. Spatial compounding has been shown to provide significant contrast resolution improvements by reducing speckle artifact and averaging out the variations in echo intensity with target interface angles. For the unfocused transmit case, spatial compounding also can regain some of the loss in lateral spatial resolution, by folding the much better axial resolution of the pulse into the lateral direction. Other techniques for improving contrast resolution, such as frequency compounding and harmonic imaging can also be employed while maintaining very short acquisition times.

Figure 9:
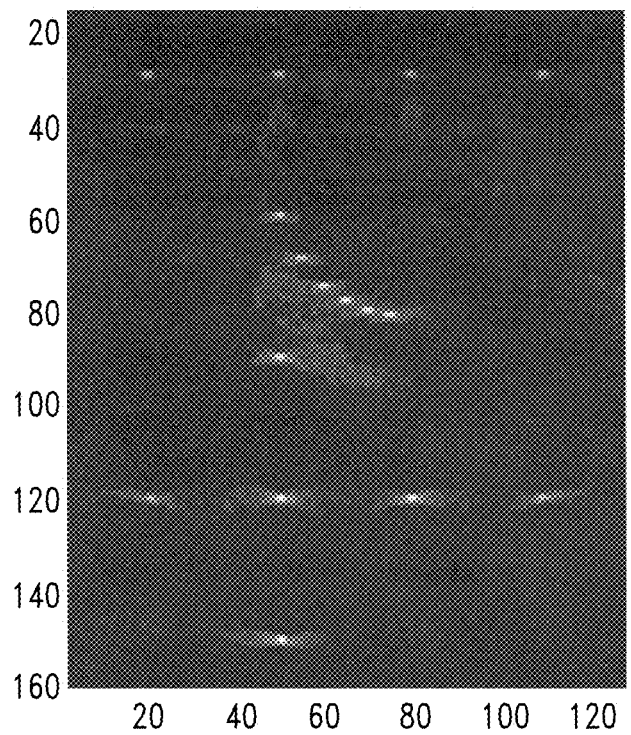
FIG. 9 is a spatially-compounded image of target points obtained from a pixel-oriented simulation of the present invention.
Figure 10:
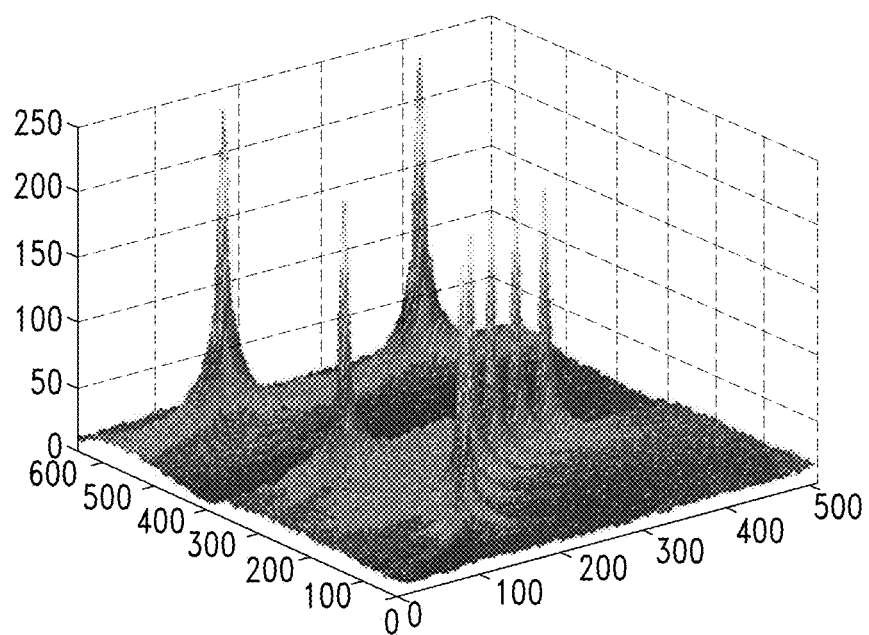
FIG. 10 is an isometric representation of the data from FIG. 9.

FIG. 9 shows a simulation that demonstrates the capability of the new system architecture for performing spatial compounding using uniform illumination imaging. The spatial compounding uses five steering angles spaced at 10 degree intervals. Comparing the spatially compounded image of FIG. 9 with the "scanline" image of FIG. 6, we see that the resolution is comparable while the side lobe levels are somewhat higher. This is remarkable in light of the fact that the acquisition time for the flash transmit image is roughly $\frac{1}{25}^{th}$ of the time for the conventional image. The lowest side lobe levels of FIG. 10 are diffuse and distributed, which is desirable for minimizing artifacts in the image. In actual living tissue, the spatially compounded image would show other benefits, reducing the angular dependence of target returns, and lowering speckle artifact. The flash transmit spatial compounding imaging method could yield higher tissue differentiation than conventional imaging at high frame rates, a combination that is not available in current high-end systems.

The short acquisition times of the flash transmit imaging method can be leveraged in other ways. Since the new system architecture provides multiple RF storage buffers, for the flash transmit method this represents multiple complete frames of data, and very high frame rates for short imaging sequences are possible. Such sequences may have important novel uses, such as 1) capturing full frame Doppler data at multiple angles for angle corrected color flow imaging, 2) shear wave imaging, where the propagation of shear wavefronts through a medium can be visualized, providing information on tissue mechanical properties, 3) elastography, where the strain response of tissue to an external force can yield information about tissue stiffness.

Furthermore, the access to a large buffer of RF frame data makes development of new algorithms straightforward, especially in the academic research community, which has been hampered by the lack of access to RF data on a clinical machine. The simple ability to trade off frame rate for dynamic range or signal to noise ratio may be a useful enhancement not easily implemented in a conventional ultrasound system.

Figure 12A:
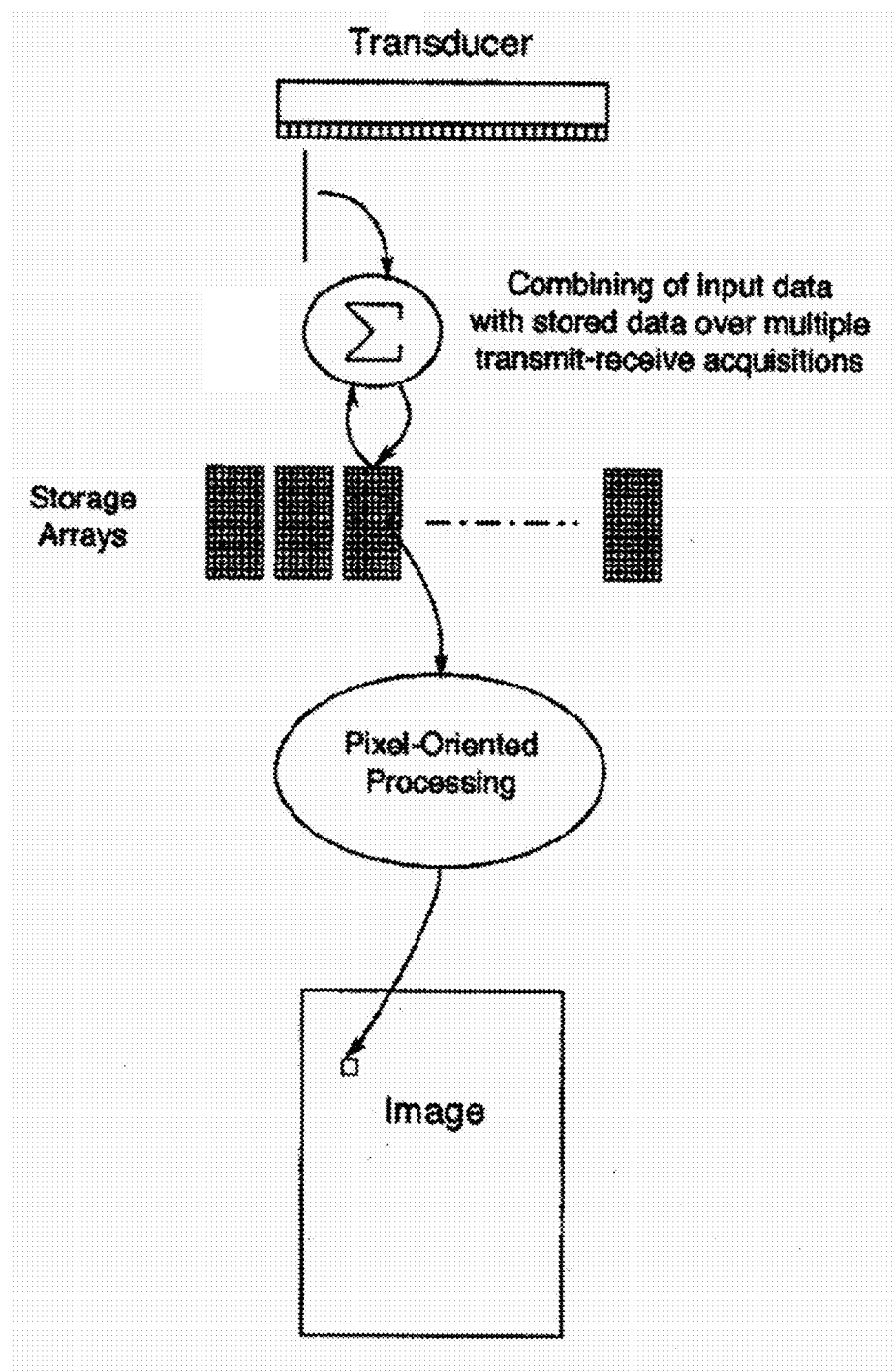
FIGS. 12A-12C illustrate alternative processing methods.
Figure 12B:
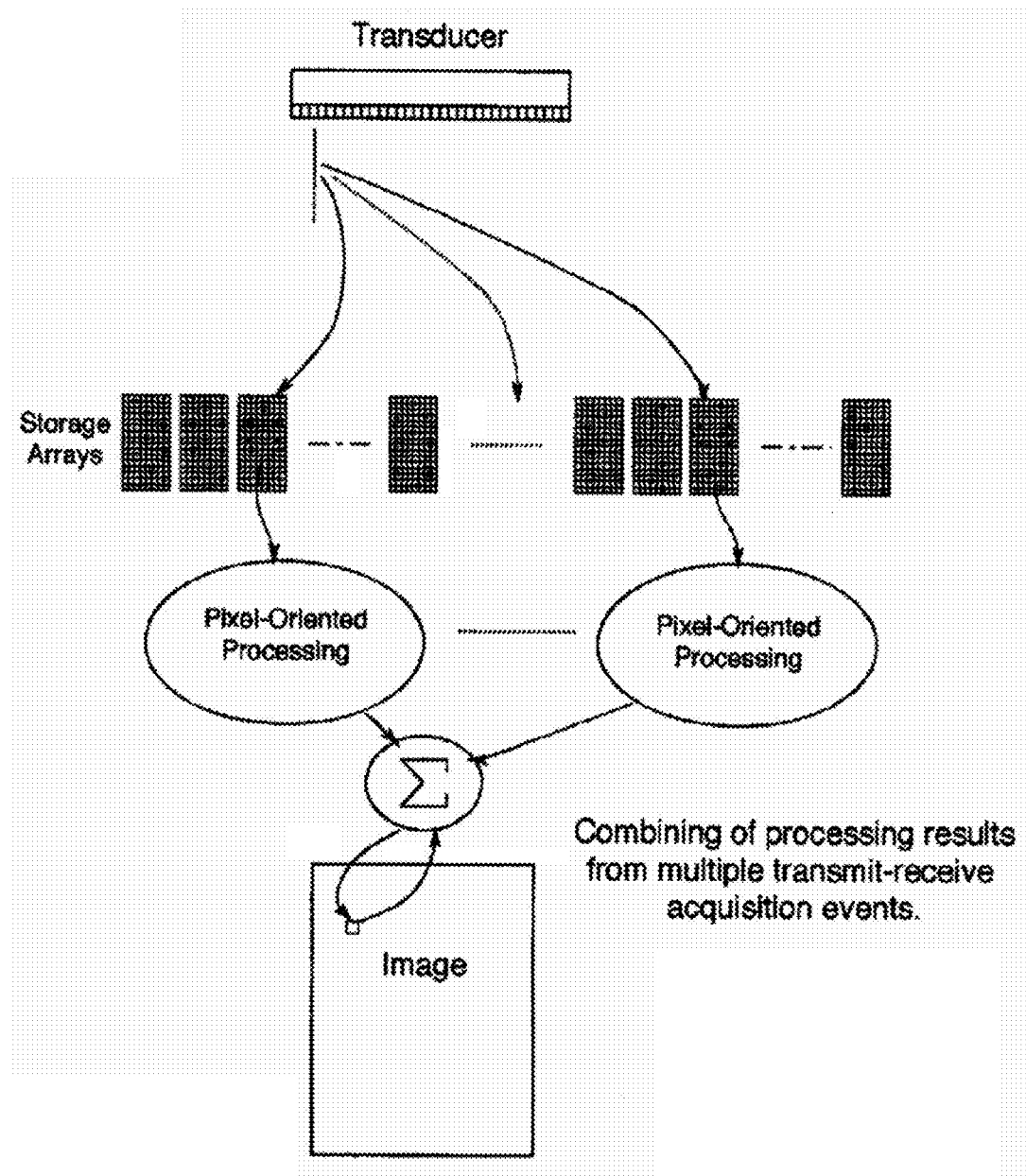
Figure 12C:
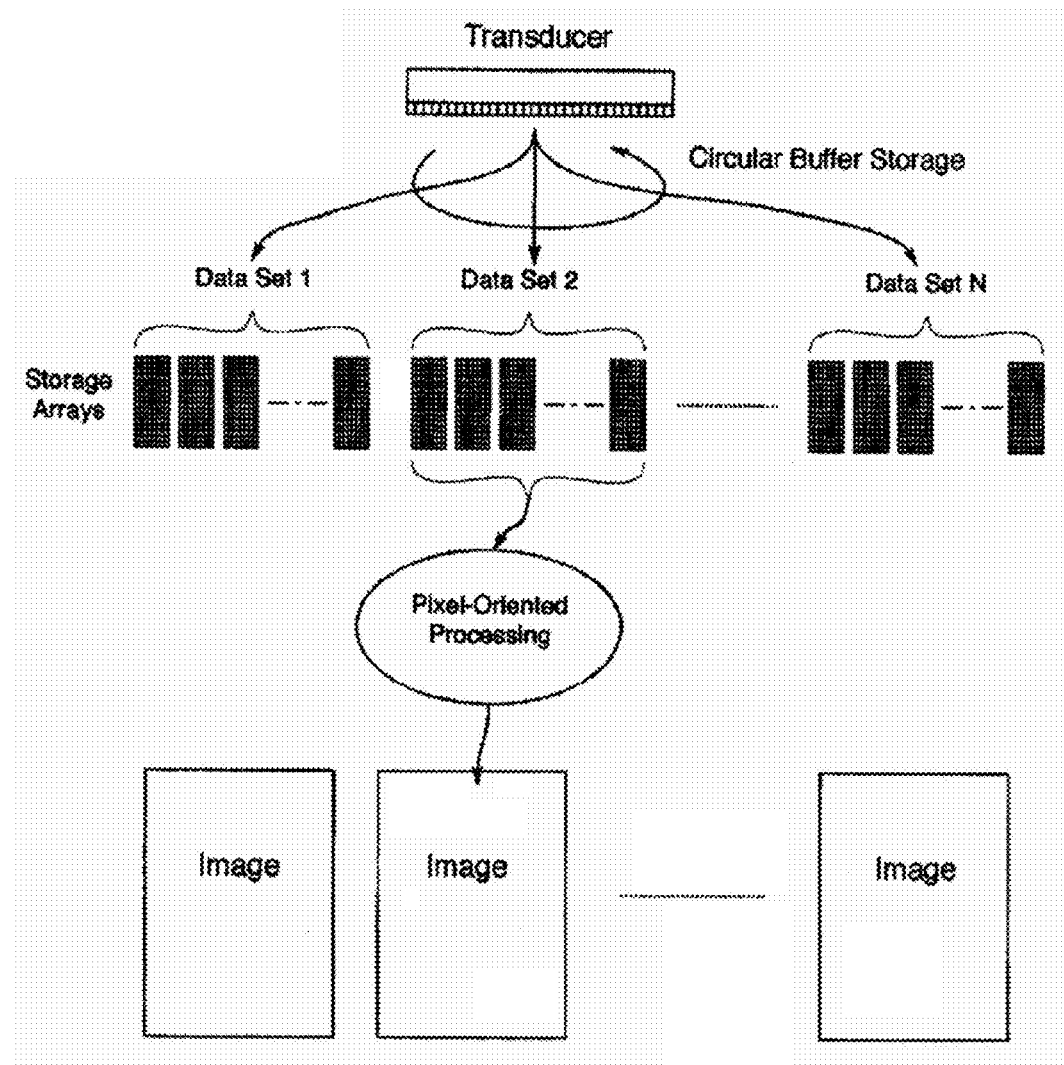

FIG. 12 summarizes the variations in the pixel oriented processing method as described above. FIG. 12A shows the combining of received echo signals with signals that have been previously stored in the storage arrays. This allows functions such as signal averaging of multiple transmit-receive acquisitions to enhance and improve signal-to-noise and dynamic range of the received signals. FIG. 12B illustrates the method of combining processed pixel signals from multiple transmit-receive acquisitions to enhance some aspect of the pixel signal. In the text above, this method was used for combining image data from transmit-receive acquisitions that interrogate media targets from various angles. This results in a spatial compounding that improves the contrast resolution of the final image. Finally, FIG. 12C illustrates the de-coupling of the processing of pixel data sets or image frames from the acquisition process. In this case, the acquisition signals required to produce an image are grouped into data sets, which consist of one or more acquisition signal arrays. The storage area is made large enough to store many of these data sets, which can be written to in a circular manner. In this method, the acquisition of echo signal data can be performed at a high rate limited only by speed of sound considerations, while the processing of pixel signals proceeds at a lower rate suitable for display. When the acquisition is stopped, all data sets can be processed at a lower rate to provide a slow motion display.

Figure 11:
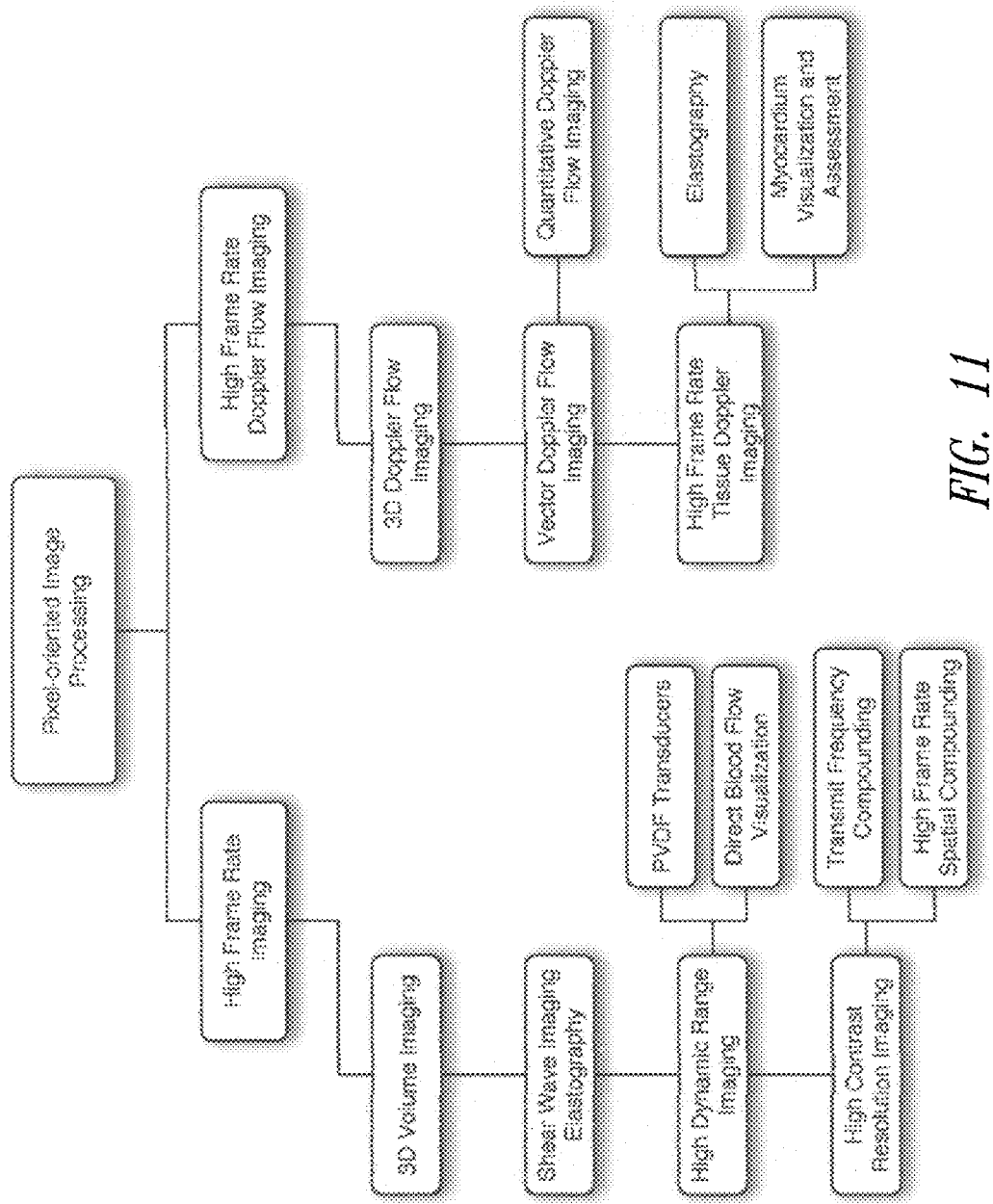
FIG. 11 is a block diagram illustrating representative applications for the pixel-oriented image processing method of the present invention.

FIG. 11 illustrates a representative selection of pixel-oriented processing applications, which is divided into two areas—high frame rate imaging, which can be used for 3D volume imaging, shear wave imaging, elastography, high dynamic range imaging, and high contrast resolution imaging, and the second area of high frame rate Doppler flow imaging, which can be used in 3D Doppler flow imaging, vector Doppler flow imaging, and high frame rate tissue Doppler imaging. Further applications in selected categories are also shown in FIG. 11.

The high frame rate applications leverage the pixel-oriented processing method combined with uniform illumination or flash transmit techniques. For 3D volume imaging, the entire volume of interest can be interrogated with one or more unfocused flash transmit pulses, allowing high real-time frame rates to be achieved, even with the combination of multiple frames for spatial or frequency compounding. For elastography imaging, the high frames rates allow the imaging of mechanical shear waves propagating through the image field, which can reveal information on the elastic properties of tissue. The high dynamic range and high contrast resolution imaging potential has been discussed above, and leverages the signal averaging and multi-frame processing capability of the pixel-oriented processing method.

The pixel-oriented processing method for 3D volume imaging is more appropriately called a voxel-oriented processing method. This is due to the fact that the output of a 3D volume scan is typically a three-dimensional cuboid containing volume elements, or voxels. The processing procedure for determining acoustic information about a specific voxel is the same as for individual pixels in a 2D image. The voxel's spatial location is mapped to a region of acquired RF data which contributes to the voxel's quantity, and a data matrix is formed. The data matrix is then processed using matrix operations to yield the quantity for the voxel. Voxel data over multiple acquisitions can also be used to obtain 3D Doppler information.

The voxel data can be displayed as two-dimensional slices through the imaging volume, or as volume-rendered perspective views. It is also possible to have simultaneous displays, where the 3D volume rendering is displayed alongside one or more two-dimensional slices determined by the system or user. Such displays are possible, since the received echo signal data can be processed with both pixel-oriented and voxel-oriented methods at the same time.

3D imaging requires more complex transducer arrays, such as mechanically swept linear arrays, or 2D arrays with large numbers of elements. In this case, the acquisition hardware may require modification. To connect a large number of transducer elements to a lesser number of transmit and receive channels, analog and/or digital multiplexing is generally employed. Some or all of this multiplexing is sometimes incorporated into the transducer housing. The multiplexers are used on transmit to select elements for forming one or more transmit beams that illuminate the 3D volume. On receive, the multiplexers are used to connect a group of transducer elements to the available receive acquisition channels. In some cases, it is appropriate to use synthetic aperture techniques to combine receive data from multiple acquisition events, thus increasing the effective number of processing channels.

The right hand side of FIG. 11 shows high frame rate Doppler flow imaging methods that also make use of the flash transmit method combined with pixel-oriented processing. It is possible to acquire flow information for the entire imaging field with only a small number of transmit/receive cycles. This 'ensemble' of acquisitions can be used to compute the average rate of change of phase at each pixel location, which is representative of the Doppler frequency shift associated with moving blood cells. Here again, the high frame rates that can be achieved using this method make practical such applications as 3D volume flow imaging, vector Doppler flow imaging (detecting both the magnitude and direction of blood flow), and tissue Doppler imaging (using the Doppler shift produced by low echogenicity moving tissue to enhance visibility). The high frame rate visualization of tissue motion also supports elastography imaging, which seeks to determine the elastic properties of tissue by observing their response to an induced mechanical displacement.

It is understood that the pixel and voxel oriented processing methods can be applied to many additional modes and applications of ultrasound imaging than are described above. Therefore, the descriptions above are not intended to limit the scope of the processing method, but rather are provided to illustrate how the method can be used to support various existing and new potential applications.

All U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. For example, the processing operations described above to generate pixel or voxel acoustic information have been implemented using matrix operations, but it is recognized that standard mathematical operations, or even hardware based processing methods could be used to accomplish some or all of the processing steps. Accordingly, the invention is not limited except as by the appended claims.

The invention claimed is:

1. A method, comprising:
generating an acoustic pulse with an ultrasound transducer and transmitting the acoustic pulse from the ultrasound transducer into an adjacent physical medium;
receiving at each of a plurality of receiving elements of the ultrasound transducer at least one echo of the acoustic pulse from the adjacent physical medium in response to the transmitting the acoustic pulse into the adjacent physical medium;
obtaining, by one or more processing units communicatively coupled to the ultrasound transducer and from each of the plurality of receiving elements, an echo signal based at least in part on the received at least one echo;
generating, by the one or more processing units, a separate respective data set array comprised of the obtained echo signals from each of the plurality of receiving elements of the ultrasound transducer, wherein each respective data set array is organized into a number of columns corresponding to the plurality of receiving elements, and wherein each column of each respective data set array consists of obtained echo signals from a corresponding one of the plurality of receiving elements;

mapping, by the one or more processing units, a first pixel or voxel from a set of pixels or voxels of a display device into a region of a respective data set array;

organizing, by the one or more processing units, the mapped region of the respective data set array into a matrix for the first pixel or voxel;

processing, by the one or more processing units, the matrix with a matrix operation to generate a signal response for the first pixel or voxel;

obtaining, by the one or more processing units, acoustic information for the first pixel or voxel based on the signal response; and repeating all of the preceding steps for each remaining pixel or voxel from the set of pixels or voxels of the display device and providing, by the one or more processing units communicatively coupled to the display device, a two-dimensional or three-dimensional image, respectively, based on the acoustic information for the set of pixels or voxels, to be displayed on the display device.

2. The method of claim 1, further comprising measuring and displaying spatial data based at least in part on the obtained acoustic information.

3. The method of claim 1, further comprising measuring and displaying temporal data based at least in part on the obtained acoustic information.

4. The method of claim 1, further comprising measuring and displaying blood flow data based at least in part on the obtained acoustic information.

5. The method of claim 1, further comprising measuring and displaying tissue displacement response to induced mechanical displacement caused by the acoustic pulse based at least in part on the obtained acoustic information.

6. The method of claim 1 further comprising storing the obtained echo signals in a memory of the one or more processing units at a rate that is higher than a rate at which the respective data set arrays are generated.

7. A system, comprising:
an ultrasound transducer adapted to generate an acoustic signal, transmit the acoustic signal into a physical medium adjacent the ultrasound transducer, receive at least one echo of the acoustic signal at a plurality of receiving elements in the ultrasound transducer from the adjacent physical medium, and obtain and store a plurality of echo signals from the plurality of receiving elements, wherein each echo signal is based at least in part on the received at least one echo of the acoustic signal;

a display device; and a processor configured to communicate with the ultrasound transducer and configured to:
  generate a separate respective data set array comprised of the stored echo signals from each of the plurality of receiving elements of the ultrasound transducer, wherein each respective data set array is organized into a number of columns corresponding to the plurality of receiving elements, and wherein each column of each respective data set array consists of obtained echo signals from a corresponding one of the plurality of receiving elements,
  map a first pixel or voxel from a set of pixels or voxels associated with the display device into a region of a respective data set array,
  organize the mapped region of the respective data set array into a matrix for the first pixel or voxel,
  process the matrix with a matrix operation to generate a signal response for the first pixel or voxel,
  obtain acoustic information for the first pixel or voxel based on the signal response, and
  repeat all of the preceding steps for each remaining pixel or voxel from the set of pixels or voxels of the display device to provide a two-dimensional or three-dimensional image, respectively, based on the acoustic information for the set of pixels or voxels;
wherein the display device is coupled to the processor and configured to display the two-dimensional or three-dimensional image.

8. The system of claim 7 wherein the processor is further configured to measure and display spatial data.

9. The system of claim 7 wherein the processor is further configured to measure and display temporal data.

10. The system of claim 7 wherein the processor is further configured to measure and display blood flow data.

11. The system of claim 7 wherein the processor is further configured to measure and display tissue response to induced mechanical displacement caused by the acoustic signal.

* * * * *